United States Patent [19]

Gullo

[11] 4,427,683

[45] Jan. 24, 1984

[54] ANTIINFLAMMATORY-2'-PYRIDYL-1'-OXIDE CARBOTHIOLATE AND CARBODITHIOATE COMPOUNDS

[75] Inventor: James M. Gullo, Perry, Ohio

[73] Assignee: SDS Biotech Corporation, Painesville, Ohio

[21] Appl. No.: 360,216

[22] Filed: Mar. 22, 1982

[51] Int. Cl.$^3$ .................. A61K 31/44; A61K 31/445; C07D 401/12

[52] U.S. Cl. .............................. 424/263; 424/248.51; 424/250; 424/267; 546/268; 546/281; 546/193; 544/124; 544/360

[58] Field of Search ....................... 546/281, 193, 268; 544/124, 36; 424/263, 267, 250, 248-251

[56] References Cited

U.S. PATENT DOCUMENTS

| | | | |
|---|---|---|---|
| 2,940,978 | 6/1960 | Brown | 546/292 |
| 3,107,994 | 10/1963 | Rawlings et al. | 71/94 |
| 3,155,671 | 11/1964 | D'Amico | 546/303 |
| 3,772,307 | 11/1973 | Kaminsky et al. | 546/294 |
| 3,984,560 | 10/1976 | Winkelmann et al. | 424/263 |
| 4,048,181 | 9/1977 | Douglass | 546/297 |
| 4,239,527 | 12/1980 | D'Amico et al. | 71/94 |

OTHER PUBLICATION

Tilles et al., Chemical Abstracts, vol. 78, No. 7, item No. 43280-u Feb. 19, 1973.

Okuda et al., Chemical Abstracts, vol. 82, No. 19, item No. 120,093x May 12, 1975.

*Primary Examiner*—Alan L. Rotman
*Attorney, Agent, or Firm*—Walter C. Danison, Jr.; Woodrow W. Ban

[57] ABSTRACT

Novel compounds of the formula:

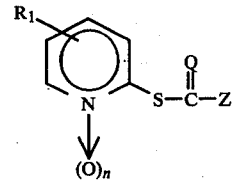

are found to be useful antiinflammatory agents.

11 Claims, No Drawings

ANTIINFLAMMATORY-2'-PYRIDYL-1'-OXIDE CARBOTHIOLATE AND CARBODITHIOATE COMPOUNDS

BACKGROUND OF THE INVENTION (1) Field of the Invention

This invention relates generally to various heterocyclic carbothiolates and carbodithioates of pyridine N-oxide which exhibit valuable antiinflammatory activity in warm-blooded animals. This invention also relates to novel pharmaceutical compositions and formulations containing the aforementioned compounds and the use of these novel pharmaceutical compositions for the treatment of inflammation, swelling, fever and like conditions in warm-blooded animals therewith.

(2) State of the Art

Various substituted S-(2'-pyridyl-1'-oxides) have heretofore been prepared and suggested for use in different ultimate applications. For example, in related U.S. Pat. Nos. 3,107,994; 3,155,671; and 4,239,527; the patentees disclose respectively haloalkenyl, benzyl- and pyridyl-S-(2'-pyridyl-1'-oxides) which compounds are useful as herbicides.

U.S. Pat. No. 3,772,307 discloses a series of pyridylthio ketones which are useful as antifungal and antibacterial agents.

In U.S. Pat. No. 3,984,560, the patentees disclose 1-alkyl-2-(pyridylthiomethyl)-5-nitro-imidazoles and 1-alkyl-2-(N-oxy-pyridylthiomethyl)-5-nitro-imidazoles having use for the treatment of protozoal diseases in mammals. U.S. Pat. No. 4,048,181 discloses a series of 2-acylamino- and 2-alkoxycarbonylamino-6-mercaptopyridine-1-oxides, disulfides thereof, and metal salts thereof having utility as antimicrobial agents, e.g., in skin cleansing detergent compositions, shampoos, hair dressings, and the like.

The patentees in U.S. Pat. No. 2,940,978 disclose certain alkyl, alkenyl and aryl thio- and dithiocarbamates of 2-mercaptopyridine N-oxide which have utility as pesticides.

None of the aforementioned disclosures, however, disclose 2'-pyridyl-1'-oxides having a heterocyclicthiolcarboxylate substituent. Moreover, no disclosure is found suggesting the use of these compounds or like compounds as antiinflammatory agents.

SUMMARY OF THE INVENTION

It has now been discovered, in accordance with the present invention, novel 2'-pyridyl-1'-oxide heterocyclic carbothiolate and carbodithiolate compounds, which possess antiinflammatory activity.

Further in accordance with the invention, methods for obtaining antiinflammatory effects in mammals by the administration of nontoxic, preselected dosages of active 2'-pyridyl-1'-oxide heterocyclic carbothiolate and carbodithioate compounds or pharmaceutically acceptable salts thereof in appropriate nontoxic pharmaceutical dosage unit forms or compositions are provided.

Still further in accordance with the present invention, stable, nontoxic pharmaceutical compositions are contemplated which are adaptable for, e.g., oral, rectal, parenteral, etc., administration and useful in the treatment, management and mitigation of inflammation conditions or disorders.

These and other similar aspects, advantages and features will be appreciated by those skilled in the art upon the reading and understanding of the specification.

DESCRIPTION OF THE PREFERRED EMBODIMENTS

Novel compounds have now been discovered which compounds are found to be highly active as antiinflammatory agents. The compounds of the present invention are 2'-pyridyl-1'-oxide heterocyclic carbothiolates and carbodithioates of the general formula I below:

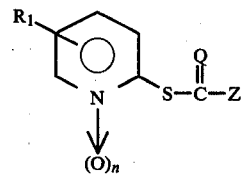

or a pharmaceutically acceptable nontoxic salt thereof wherein $R_1$ is hydrogen, alkyl, halogen or alkoxy, n is 0 or 1, Q is sulfur or oxygen and Z represents

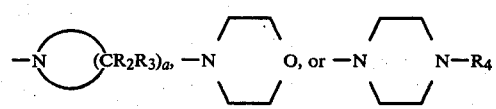

where a is 4–7 and $R_2$, $R_3$, and $R_4$ all independently represent hydrogen or alkyl. Also to be included within the scope of the present invention as active antiinflammatory agents are the compounds of the general formula I above wherein Z represents $NR_5R_6$ where $R_5$ and $R_6$ independently represent hydrogen, alkyl or aryl.

As used throughout the instant specification and claims, the expression "alkyl" is inclusive of straight and branched chain carbon-carbon linkages and represents $C_1$–$C_5$ atoms. The expression "pharmaceutically acceptable nontoxic salts," as used herein, is intended to include those salts capable of being formed with the instant compounds and substituted derivatives thereof in accordance with the invention without materially altering the chemical structure or pharmacological properties of the parent compounds.

As will be apparent to those skilled in the art, the heterocyclic rings defined above can contain two (2) or more alkyl substituents which polyalkyl-heterocyclic rings can exist as different structural isomers, e.g., cis- and trans-2,5-dimethyl-1-pyrrolidinecarbothiolate. All possible structural isomers of the compounds of the present invention are, therefore, to be included within the scope of the present invention.

The compounds of the present invention may be prepared by alternative methods previously employed in the synthesis of analogous compounds. However, the compounds of the present invention are prepared by the reaction of the appropriately substituted sodium salt of 2-mercaptopyridine-1-oxide with the appropriate carbonyl chloride or thiocarbonyl chloride in tetrahydrofuran to give the desired 2'-pyridyl-1'-oxide heterocyclic carbothiolate and carbodithioate. A more detailed description of this procedure is set out in the example below.

As previously indicated, the compounds of the present invention evidence antiinflammatory effects in warm-blooded animals. It will be appreciated that the specific response elicited upon administration of the compounds of the present invention to an animal species in need thereof will vary depending upon the specific structure of the administered compound, the unit dosage, dosage regimen and mode of administration, as well as the particular mammalian species involved. The preferred compounds for use in the antiinflammatory compositions and methods of the present invention are compounds of the above general formula I wherein Q is oxygen, Z is pyrrolidine or dimethylpyrrolidine (cis and trans) and $R_1$ is hydrogen or methyl. The most preferred compound is 2'-pyridyl-1'-oxide cis-2,5-dimethyl-1-pyrrolidinecarbothiolate.

In accordance with the practices of the present invention, the active compounds of the invention may be administered alone or in combination with each other or administered in admixture with pharmaceutical diluents, carriers, excipients or adjuvants suitably selected with respect to the intended route of administration and conventional pharmaceutical practices. For instance, for oral administration in the form of tablets or capsules, the active compound or compounds of the invention may be combined with such excipients as starch, lactose, sucrose, cellulose, magnesium stearate, and the like. Similarly, injectable dosage unit forms may be utilized to accomplish intravenous, intramuscular or subcutaneous administration and, for such parental administration, suitable sterile solutions or nonaqueous solutions or suspensions, optionally containing appropriate solutes to effectuate isotonicity, will be employed. Other suitable adjuvants and dosage forms will be apparent to those skilled in the art.

Compounds of the invention or compositions thereof may be administered to warm-blooded animals, i.e., mammals including, for instance, mice, rats, guinea pigs, dogs and other domesticated animals, or humans. Dosages sufficient to elicit the above-indicated antiinflammatory response will generally range between about 1 to 300 mg/kg/day in laboratory mice based upon body weight, and preferably, between about 10 to about 200 mg/kg/day. The foregoing dosages will normally be administered in 3 or 4 divided doses, depending upon the desired dosage regimen. Of course, the actual effective dosage to be administered will vary, depending upon the specific compound involved, as well as the age, weight and responsiveness of the particular animal species.

The following nonlimiting examples are afforded in order that those skilled in the art may more readily understand the present invention and specific preferred embodiments thereof with respect to the preparation of starting materials, intermediates and compounds in accordance with the foregoing description.

EXAMPLE 1

2'-Pyridyl-1'-Oxide Cis-2,5-Dimethyl-1-Pyrrolidinecarbothiolate

Into a 500 mL. flask equipped with a magnetic stirrer and thermometer were placed 10.2 g. (0.08 m.) of 2-mercaptopyridine-N-oxide, 300 mL. of tetrahydrofuran (THF) and 3.8 g. (0.08 m.) of 50% sodium hydride. After the sodium hydride reacted, 11.3 g. (0.07 m.) of cis-2,5-dimethyl-1-pyrrolidinecarbonyl chloride was added to the flask. There was no exotherm. A heating mantle and condenser were equipped to the flask and the contents were then heated to reflux for three hours, after which they were cooled and filtered. Most of the THF was evaporated under vacuum and the resulting slurry was poured into water.

The aqueous slurry was extracted with chloroform. The chloroform was removed under vacuum from the extract. The resulting oil was dissolved in a 50:50 mixture of hexane-ethyl acetate. This solution was passed through a silica gel dry column. The second band from the bottom was eluted. From this eluate was obtained 6.8 g. (35.5% yield) of product. The NMR integrated correctly for the desired compound. M.P. 95°–97° C.

EXAMPLE 2

2'-Pyridyl-1'-Oxide 1-Pyrrolidinecarbothiolate

Into a 500 mL. flask equipped with magnetic stirrer, heating mantle, thermometer and condenser were added 10.2 g. (0.08 m.) of 2-mercaptopyridine-N-oxide, 300 mL. of THF and 3.8 g. (0.08 m.) of a 50% sodium hydride in an oil dispersion. After the sodium hydride reacted, 9.35 g. (0.07 m.) of 1-pyrrolidinecarbonyl chloride was added to the flask resulting in a temperature rise of from 35.5° to 37°. The contents were heated at reflux for three hours, cooled and the THF evaporated under vacuum. The resulting oily material was passed through a silica gel dry column using a 50:50 mixture of hexane-ethyl acetate. The third band from the bottom was eluted. The resulting oily material was slurried with 30 mL. of hot hexane twice. There was obtained 6.0 g. (38.2% yield) of material (11685-122-26) melting 105°–106°. The NMR (R16178) integrated correctly for the desired compound.

EXAMPLE 3

2'-Pyridyl-1'-oxide 1-hexamethyleneiminecarbothiolate

Into a 500 mL. flask equipped with a magnetic stirrer, heating mantle and condenser were added 12.7 g. (0.1 m.) of 2-mercaptopyridine-N-oxide, 300 mL. of THF and 4.8 g. (0.1 m.) of 50% sodium hydride oil dispersion. After the sodium hydride reacted, 13.8 g. (0.085 m.) of 1-hexamethyleneiminecarbonyl chloride was added to the flask and the contents heated at reflux for three hours, then cooled and the THF evaporated off under vacuum. The solid material was slurried with 1000 mL. of hot hexane. The resulting solid was dissolved in 1900 mL. of ethyl ether and filtered. The solution was cooled in dry ice and the precipitated material was filtered. There was obtained 9.7 g. (45.2% yield) of material (11685-125-16) melting 97°–98°. The NMR (R16254) integrated correctly for the desired product.

The following compounds of the present invention may be prepared by utilizing synthesis methods analogous to the foregoing examples.

2'-pyridyl-1'-oxide-cis-2,5-dimethyl-1-pyrrolidinecarbodithioate;

2'-pyridyl-1'-oxide 1-trans-2,5-dimethylpyrrolidinecarbothiolate;

2'-pyridyl-1'-oxide 1-pyrrolidinecarbodithioate;

4'-methyl-2'-pyridyl-1'-oxide cis-2,5-dimethyl-1-pyrrolidinecarbothiolate;

2'-pyridyl-1'-oxide cis-2,6-dimethyl-1-piperidinecarbothiolate;

2'-pyridyl-4'-oxide 1-morpholinecarbothiolate;

2'-pyridyl-1'-oxide 4-methyl-1-piperazinecarbothiolate;

5'-bromo-2'-pyridyl-1'-oxide cis-2,5-dimethyl-1-pyrrolidinecarbothiolate.

EXAMPLE 4

Antiinflammatory Assay

Antiinflammatory activity, i.e., effectiveness in the prevention and inhibition of granuloma tissue formation, is demonstrated by relative inhibition of carregeenin-induced edema as determined by the diminution of experimental edema induced in the hind paw of a rat by the invention of carregeenin. The procedure employed is a modification of the method of Winter et al, *Proc. Soc. Exptl. Biol. Med.*, 111:544 (1962). The device used for measurement of the paw volume is an adaptation of the water displacement procedure described by Adamkiewicz et al, *Can. J. Biochem. Physiol.*, 33:332 (1955). Test compounds were administered orally, one hour prior to the intraplanter injection of 0.05 mL. of sterile 1.0% solution of carregeenin into the left hind paw of male rates (Long Evans strain) weighing between about 130–200 g. At peak swelling time (3 hrs.) the volume of edema was calculated by differential paw volumes.

Results of this assay showed the compound of Example 1 to give 50% reduction of edema for a 200 mg/kg dose.

The compound of Example 1 was further tested to determine its $ED_{50}$ value. The $ED_{50}$ value is defined as that dose which reduced edema formation by about 25% or more compared with the mean control response (parallel run) in 50% of the animals. The compound of Example 1 gave an $ED_{50}$ value of 10–20 mg/kg.

EXAMPLE 5

The compound of Example 1 was subjected to a secondary screen designated the adrenalectomized assay. In this series of tests, the method used was identical to that described above, except that the animals used were adrenalectomized several days prior to assay. The results of this assay for the compound of Example 1 showed the compound to be active at 3 mg/kg.

EXAMPLE 6

The compound of Example 1 was further subjected to advanced evaluations. Specifically, in view of the interesting activity of this compound, the compound was further subjected to the adjuvant-induced arthritis test. This test requires one month (from day 0 to day 31). In the first 17 days (0–17), the disease is in a developing stage; while for the remainder of the month (18–31), the disease is fully developed. The method employed is that essentially described by Newbould, *Brit. J. Pharmacol.*, 21:127 (1963). The results of this test showed that the compound of Example 1 was active at 10 mg/kg.

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove may be applicable as a consequence of variations and responsiveness of the mammal treated, severity of the inflammation or like condition, dosage related adverse effects, if any, observed an analogous considerations. Likewise, specific pharmacological responses observed may vary depending upon the particular active compounds selected or whether difference active compounds are used in combination or in the presence of suitable pharmaceutical carriers, as well as the type of formulations and mode of administration employed, in such expected variations or differences in results are contemplated in accordance with the features and practices of the present invention. It is intended, therefore, that the invention be limited only by the scope of the claims which allow.

What is claimed is:

1. A compound of the formula

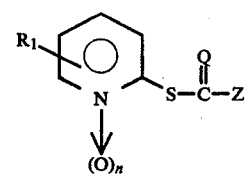

or a pharmaceutically acceptable nontoxic salt thereof wherein $R_1$ is hydrogen, alkyl, halogen or alkoxy, n is 1, Q is sulfur or oxygen and Z represents

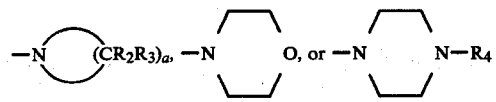

where a is 4–6 and $R_2$, $R_3$ and $R_4$ independently represent hydrogen or alkyl; wherein the terms alkyl and alkoxy as used herein are inclusive of straight and branch chain carbon-carbon linkages and represent 1 to 5 carbon atoms.

2. The compound as defined in claim 1 wherein said compound is 2'-pyridyl-1'-oxide cis-2,5-dimethyl-1-pyrrolidinecarbodithioate, 2'-pyridyl-1'-oxide 1-pyrrolidinecarbodithioate, 4'-methyl-2'-pyridyl-1'-oxide cis-2,5-dimethyl-1pyrrolidinecarbothiolate, 2'-pyridyl-1'-oxide cis-2,6-dimethyl-1-piperidinecarbothiolate, 2'-pyridyl-1'-oxide 1-morpholinecarbothiolate, 2'-pyridyl-1'-oxide 4-methyl-1-piperazinecarbothiolate, 5'-bromo-2'-pyridyl-1'-oxide cis-2,5-dimethyl-1-pyrrolidinecarbothiolate, 2'-pyridyl-1'-oxide 1-hexamethyleneiminecarbothiolate and 2'-pyridyl-1'-oxide 1-trans-2,5-dimethylpyrrolidinecarbothiolate.

3. The compound as defined in claim 1 wherein said compound is 2'-pyridyl-1'-oxide cis-2,5-dimethyl-1-pyrrolidinecarbothiolate.

4. A pharmaceutical antiinflammatory composition in dosage unit form comprised of an inert pharmaceutical carrier and an active ingredient, the active ingredient of which consists of a nontoxic antiinflammatory effective amount of a compound of the formula:

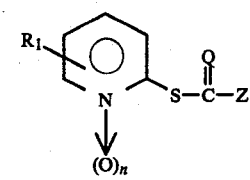

or a pharmaceutically acceptable nontoxic salt thereof wherein $R_1$ is hydrogen, alkyl, halogen or alkoxy, n is 1, Q is sulfur or oxygen and Z represents $NR_5R_6$,

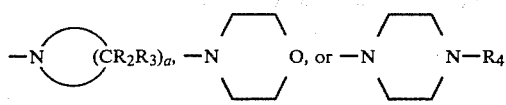

where a is 4–6, $R_2$ $R_3$ and $R_4$ independently represent hydrogen or alkyl and $R_5$ and $R_6$ independently represent hydrogen, alkyl or phenyl; wherein the terms alkyl and alkoxy as used herein as inclusive of straight and branch chain carbon-carbon linkages and represent 1 to 5 carbon atoms.

5. A composition as defined in claim 4 wherein the active ingredient is the compound 2'-pyridyl-1'-oxide cis-2,5-dimethyl-1-pyrrolidinecarbodithioate, 2'-pyridyl-1'-oxide 1-pyrrolidinecarbodithioate, 4'-methyl-2'-pyridyl-1'-oxide cis-2,5-dimethyl-1-pyrrolidinecarbothiolate, 2'-pyridyl-1'-oxide cis-2,6-dimethyl-1-piperidinecarbothiolate, 2'-pyridyl-1'-oxide 1-morpholinecarbothiolate, 2'-pyridyl-1'-oxide 4-methyl-1-piperazinecarbothiolate, 5'-bromo-2'-pyridyl-1'-oxide cis-2,5-dimethyl-1-pyrrolidinecarbothiolate, 2'-pyridyl-1'-oxide 1-hexamethyleneiminecarbothiolate and 2'-pyridyl-1'-oxide 1-trans-2,5-dimethylpyrrolidinecarbothiolate.

6. A composition as defined in claim 4 wherein the active ingredient is the compound 2'-pyridyl-1'-oxide cis-2,5-dimethyl-1-pyrrolidinecarbothiolate.

7. A composition as defined in claims 4 or 5 wherein the antiinflammatory amount is within the range of about 10 to 200 mg/kg/day.

8. A method of obtaining an antiinflammatory effect in a mammal in need thereof comprising administering thereto an antiinflammatory effective amount of a compound of the formula:

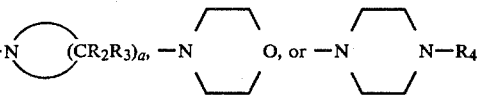

or a pharmaceutically acceptable nontoxic salt thereof wherein $R_1$ is hydrogen, alkyl, halogen or alkoxy, n is 1, Q is sulfur or oxygen and Z represents

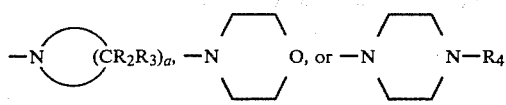

where a is 4–6, $R_2$ $R_3$ and $R_4$ independently represent hydrogen or alkyl and $R_5$ and $R_6$ independently represent hydrogen, alkyl or phenyl; wherein the terms alkyl and alkoxy as used herein are inclusive of straight and branch chain carbon-carbon linkages and represent 1 to 5 carbon atoms.

9. A method as defined in claim 8 wherein said compound is 2'-pyridyl-1'-oxide cis-2,5-dimethyl-1-pyrrolidinecarbodithioate, 2'-pyridyl-1'-oxide 1-pyrrolidinecarbodithioate, 4'-methyl-2'-pyridyl-1'-oxide cis-2,5-dimethyl-1pyrrolidinecarbothiolate, 2'-pyridyl-1'oxide cis-2,6-dimethyl-1-piperidinecarbothiolate, 2'-pyridyl-1'-oxide 1-morpholinecarbothiolate, 2'-pyridyl-1'-oxide 4-methyl-1-piperazinecarbothiolate, 5'-bromo-2'-pyridyl-1'-oxide cis-2,5-dimethyl-1-pyrrolidinecarbothiolate and 2'-pyridyl-1'-oxide 1-hexamethyleneiminecarbothiolate.

10. A method as defined in claim 8 wherein said compound is 2'-pyridyl-1'-oxide cis-2,5-dimethyl-1-pyrrolidinecarbothiolate.

11. A method as defined in claims 8 or 9 wherein the antiinflammatory effective amount is within the range of about 10 to about 200 mg/kg/day.

* * * * *